(12) United States Patent
Pavcnik et al.

(10) Patent No.: US 8,444,666 B2
(45) Date of Patent: May 21, 2013

(54) RETRIEVABLE FILTER

(75) Inventors: Dusan Pavcnik, Portland, OR (US);
Brian C. Case, Bloomington, IN (US);
John A. Kaufman, Lake Oswego, OR (US); Michael L. Garrison, Bloomington, IN (US); Jacob A. Flagle, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 3559 days.

(21) Appl. No.: 10/662,216

(22) Filed: Sep. 12, 2003

(65) Prior Publication Data
US 2004/0193209 A1 Sep. 30, 2004

Related U.S. Application Data

(60) Provisional application No. 60/410,236, filed on Sep. 12, 2002.

(51) Int. Cl.
*A61B 17/00* (2006.01)
*A61F 2/06* (2006.01)
*A61F 2/82* (2006.01)

(52) U.S. Cl.
USPC .......................... 606/200; 623/1.12; 623/1.15

(58) Field of Classification Search
USPC ................. 606/200, 108, 194, 198; 623/1.11, 623/1.12
See application file for complete search history.

(56) References Cited

U.S. PATENT DOCUMENTS

| | | |
|---|---|---|
| 3,540,431 A | 11/1970 | Mobin-Uddin |
| 3,654,773 A | 4/1972 | White |
| 3,810,367 A | 5/1974 | Peterson |
| 3,952,747 A | 4/1976 | Kimmell, Jr. |
| 4,218,783 A | 8/1980 | Reul et al. |
| 4,425,908 A | 1/1984 | Simon |

(Continued)

FOREIGN PATENT DOCUMENTS

| | | |
|---|---|---|
| DE | 3417738 A1 | 11/1984 |
| DE | 4030998 A1 | 4/1992 |

(Continued)

OTHER PUBLICATIONS

N. Nakagawa, *A Retrievable Nitinol Vena Cava Filter: Experimental and Initial Clinical Results*, Journal of Vascular and Interventional Radiology, May-Jun. 1995, pp. 507-512.

(Continued)

*Primary Examiner* — Tuan V Nguyen
(74) *Attorney, Agent, or Firm* — Brinks Hofer Gilson & Lione

(57) ABSTRACT

A filter may have an apical hub and a plurality of divergent legs. A first attachment member may be separate from, but attached to the second end of at least one of the plurality of divergent legs. A second attachment member may be separate from, but attached to a stent. The first and second attachment members may be separate from, but attachable to one another to releasably attach the filter to the stent. One of the first attachment member and the second attachment member may include an attachment wire that is positioned in a lumen of a tubular member or one of the first attachment member and the second attachment member may comprise a cannula. In some implementations, an upward motion applied to the retrieval connection member may disengage at least one attachment wire of the first attachment member from the second attachment member.

30 Claims, 7 Drawing Sheets

U.S. PATENT DOCUMENTS

| | | |
|---|---|---|
| 4,494,531 A | 1/1985 | Gianturco |
| 4,580,568 A | 4/1986 | Gianturco |
| 4,619,246 A | 10/1986 | Molgaard-Nielsen et al. |
| 4,643,184 A | 2/1987 | Mobin-Uddin |
| 4,655,771 A | 4/1987 | Wallsten |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,800,882 A | 1/1989 | Gianturco |
| 4,817,600 A | 4/1989 | Herms et al. |
| 4,832,055 A | 5/1989 | Palestrant |
| 4,873,978 A | 10/1989 | Ginsburg |
| 4,954,126 A | 9/1990 | Wallsten |
| 4,969,891 A | 11/1990 | Gewertz |
| 5,035,706 A | 7/1991 | Giantureo et al. |
| 5,041,126 A | 8/1991 | Gianturco |
| 5,059,205 A | 10/1991 | El-Nounou et al. |
| 5,104,399 A | 4/1992 | Lazarus |
| 5,108,418 A | 4/1992 | Lefebvre |
| 5,133,733 A | 7/1992 | Rasmussen et al. |
| 5,147,379 A | 9/1992 | Sabbaghian et al. |
| 5,152,777 A | 10/1992 | Goldberg et al. |
| 5,174,295 A | 12/1992 | Christian et al. |
| 5,234,458 A | 8/1993 | Metais |
| 5,242,462 A | 9/1993 | El-Nounou et al. |
| 5,282,824 A | 2/1994 | Gianturco |
| 5,314,444 A | 5/1994 | Gianturco |
| 5,324,304 A | 6/1994 | Rasmussen |
| 5,334,217 A | 8/1994 | Das |
| 5,344,427 A | 9/1994 | Cottenceau et al. |
| 5,350,398 A | 9/1994 | Pavcnik et al. |
| 5,358,518 A | 10/1994 | Camilli |
| 5,370,657 A | 12/1994 | Irie |
| 5,375,612 A | 12/1994 | Cottenceau et al. |
| 5,380,320 A | 1/1995 | Morris |
| 5,383,887 A | 1/1995 | Nadal |
| 5,387,235 A | 2/1995 | Chuter |
| 5,411,552 A | 5/1995 | Andersen et al. |
| 5,423,829 A | 6/1995 | Pham et al. |
| 5,456,713 A | 10/1995 | Chuter |
| 5,480,424 A | 1/1996 | Cox |
| 5,500,014 A | 3/1996 | Quijano et al. |
| 5,522,836 A | 6/1996 | Palermo |
| 5,527,355 A | 6/1996 | Ahn |
| 5,540,680 A | 7/1996 | Guglielmi et al. |
| 5,562,724 A | 10/1996 | Vorwerk et al. |
| 5,562,726 A | 10/1996 | Chuter |
| 5,601,595 A | 2/1997 | Smith |
| 5,607,465 A | 3/1997 | Camilli |
| 5,626,605 A | 5/1997 | Irie et al. |
| 5,634,942 A | 6/1997 | Chevillon et al. |
| 5,643,254 A | 7/1997 | Scheldrup |
| 5,643,312 A | 7/1997 | Fischell et al. |
| 5,669,905 A | 9/1997 | Scheldrup et al. |
| 5,681,347 A | 10/1997 | Cathcart et al. |
| 5,693,084 A | 12/1997 | Chuter |
| 5,693,085 A | 12/1997 | Buirge et al. |
| 5,709,704 A | 1/1998 | Nott et al. |
| 5,725,550 A | 3/1998 | Nadal |
| 5,746,767 A | 5/1998 | Smith |
| 5,755,777 A | 5/1998 | Chuter |
| 5,755,790 A | 5/1998 | Chevillon et al. |
| 5,814,064 A | 9/1998 | Daniel et al. |
| 5,824,061 A | 10/1998 | Quijano et al. |
| 5,827,324 A | 10/1998 | Cassell et al. |
| 5,836,969 A | 11/1998 | Kim et al. |
| 5,840,081 A | 11/1998 | Andersen et al. |
| 5,843,170 A | 12/1998 | Ahn |
| 5,843,176 A | 12/1998 | Weier |
| 5,848,964 A | 12/1998 | Samuels |
| 5,853,420 A | 12/1998 | Chevillon et al. |
| 5,855,597 A | 1/1999 | Jayaraman |
| 5,855,601 A | 1/1999 | Bessler et al. |
| 5,907,893 A | 6/1999 | Zadno-Azizi et al. |
| 5,911,704 A | 6/1999 | Humes |
| 5,938,683 A | 8/1999 | Lefebvre |
| 5,941,896 A | 8/1999 | Kerr |
| 5,968,071 A | 10/1999 | Chevillon et al. |
| 5,976,172 A | 11/1999 | Homsma et al. |
| 5,984,947 A | 11/1999 | Smith |
| 6,001,118 A | 12/1999 | Daniel et al. |
| 6,007,558 A | 12/1999 | Ravenscroft et al. |
| 6,013,093 A | 1/2000 | Nott et al. |
| 6,036,720 A | 3/2000 | Abrams et al. |
| 6,063,113 A | 5/2000 | Kavteladze et al. |
| 6,067,491 A | 5/2000 | Takahashi |
| 6,080,178 A | 6/2000 | Meglin |
| 6,083,239 A | 7/2000 | Addis |
| 6,086,577 A | 7/2000 | Ken et al. |
| 6,096,053 A | 8/2000 | Bates |
| 6,110,201 A | 8/2000 | Quijano et al. |
| 6,126,673 A | 10/2000 | Kim et al. |
| 6,126,686 A | 10/2000 | Badylak et al. |
| 6,146,396 A | 11/2000 | Konya et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,603 B1 | 1/2001 | Leslie et al. |
| 6,168,614 B1 | 1/2001 | Andersen et al. |
| 6,171,327 B1 | 1/2001 | Daniel et al. |
| 6,183,495 B1 | 2/2001 | Lenker et al. |
| 6,193,739 B1 | 2/2001 | Chevillon et al. |
| 6,200,336 B1 | 3/2001 | Pavcnik et al. |
| 6,214,025 B1 | 4/2001 | Thistle et al. |
| 6,217,600 B1 | 4/2001 | DiMatteo |
| 6,221,091 B1 | 4/2001 | Khosravi |
| 6,231,581 B1 | 5/2001 | Shank et al. |
| 6,231,589 B1 | 5/2001 | Wessman et al. |
| 6,241,746 B1 | 6/2001 | Bosma et al. |
| 6,241,763 B1 | 6/2001 | Drasler et al. |
| 6,245,089 B1 | 6/2001 | Daniel et al. |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Witcher et al. |
| 6,280,467 B1 | 8/2001 | Leonhardt |
| 6,287,334 B1 | 9/2001 | Moll et al. |
| 6,315,793 B1 | 11/2001 | Bokros et al. |
| 6,319,281 B1 | 11/2001 | Patel |
| 6,325,815 B1 | 12/2001 | Kusleika et al. |
| 6,327,772 B1 | 12/2001 | Zadno-Azizi et al. |
| 6,328,755 B1 | 12/2001 | Marshall |
| 6,342,062 B1 | 1/2002 | Suon et al. |
| 6,342,063 B1 * | 1/2002 | DeVries et al. ............... 606/200 |
| 6,416,530 B2 | 7/2002 | DeVries et al. |
| 6,506,205 B2 | 1/2003 | Goldberg et al. |
| 6,712,834 B2 * | 3/2004 | Yassour et al. ............... 606/200 |
| 2001/0011187 A1 | 8/2001 | Pavcnik et al. |
| 2001/0023358 A1 | 9/2001 | Tsukernik |
| 2001/0039450 A1 | 11/2001 | Pavcnik et al. |
| 2001/0041928 A1 | 11/2001 | Pavcnik et al. |
| 2002/0032414 A1 | 3/2002 | Ragheb et al. |
| 2002/0055767 A1 | 5/2002 | Forde et al. |
| 2002/0116024 A1 * | 8/2002 | Goldberg et al. ............. 606/200 |
| 2004/0088001 A1 | 5/2004 | Bosma et al. |

FOREIGN PATENT DOCUMENTS

| | | |
|---|---|---|
| FR | 2666980 | 9/1990 |
| WO | WO 95/09567 | 4/1995 |
| WO | WO 98/23322 | 6/1998 |
| WO | WO 00/66031 | 11/2000 |
| WO | WO 02 11812 A | 2/2002 |

OTHER PUBLICATIONS

Z. Y Xian et al., *In Vitro Evaluation of a New Temporary Venous Filter: The Spring Filter*, CardioVascular and Interventional Radiology, Springer-Verlag, New York (1995) vol. 18, pp. 315-320.

B. S. Kuszyk et al., *Subcutaneously Tethered Temorary Filter: Pathologic Effects in Swine*, Journal of Vascular and Interventional Radiology, Nov.-Dec., 1995, pp. 895-202.

C. Cope et al., *Temporary Use of a Bird's Nest Filter During Iliocaval Thrombolysis*, Radiology, 1996, pp. 765-767.

G. Bovyn et al., *The Tempofifter; A Multicenter Study of a New Temporary Caval Filter Implantable for up to Six Weeks*, Annals of Vascular Surgery, vol. II, No. 5 1997, pp. 520-528.

L. D. Vos et al., *The Gunther Temporary Inferior Vena Cava Filter for Short-Term Protection Against Pulmonary Embolism*, CardioVascular and Interventional Radiology, Springer-Verlag, New York 1997, vol. 20, pp. 91-97.

H. Lorch et al., *In Vitro Studies of Temporary Vena Cava Filters*, CardioVascular and Interventional Radiology, Springer-Verlag, New York 1998, vol. 21, pp. 146-150.

M. Zwaan et al., *Clinical Experience with Temporary Vena Caval Filters*, Journal of Vascular and Interventional Radiology, 1998, vol. 9, pp. 594-601.

J. Hosaka et al., *In Vitro Function of an Adjustable Temporary Venous Spring Filter*, Academy of Radiology, Sep. 1998, vol. 5, No. 9, pp. 620-625.

S. F. Millward et al., *Temporary and Retrievable Inferior Vena Cava Filters: Current Status*, CardioVascular and Interventional Radiology, May-Jun. 1998, vol. 9, No. 3, pp. 381-387.

G. Lund et al., *A New Vena Caval Filter for Percutaneous Placement and Retrieval: Experimental Study*, Radiology 1984, vol. 152, pp, 369-372.

D. W. Hunter et al., *Retrieving the Amplatz Retrievable Vena Cava Filter*, CardioVascular and Interventional Radiology, Springer-Verlag New York 1987, vol. 10, pp. 32-36.

G. P. Teitelbaum et al., *Insertion and Recovery of a Ne Retrievable Vena Caval Filter*, Investigative Radiology, Jul. 1988, vol. 23, pp. 527-533.

J. Neuerburg et al., *New Retrievable Percutaneous Vena Cava Filter: Experimental In Vitro and In Vivo Evaluation*, CardioVascular, Springer-Verlag New York 1993, vol. 16, pp. 224-229.

T. Irie et al., *Retrievable IVC Filter: Preliminary In Vitro and In Vivo Evaluation*, Journal of Vascular and Interventional Radiology, May-Jun. 1995, vol. 6, pp. 449-454.

T. M. Vesely et al, *Preliminary Investigation of the Erie Inferior Vena Caval Filter*, Journal of Vascular and Interventional Radiology, Jul.-Aug. 1996, vol. 7, pp. 529-535.

A. Dibie et al., *In Vivo Evaluation of a Retrievable Vena Cafa Filter—The Dibie-Musset Filter: Experimental Results*, CardioVascular and Interventional Radiology, Springer-Verlag, New York 1998, vol. 21, pp. 151-157.

G. S. Dorfman, *Percutaneous Inferior Caval Filters*, Radiology 1990, vol. 174, pp. 987-992.

S. Kadir, *Stent Placement for Caval and Tracheobronichial Stenoses*, Current Practice of Interventional Radiology, B. C. Decker Inc. Philadelphia, pp. 208-212.

\* cited by examiner

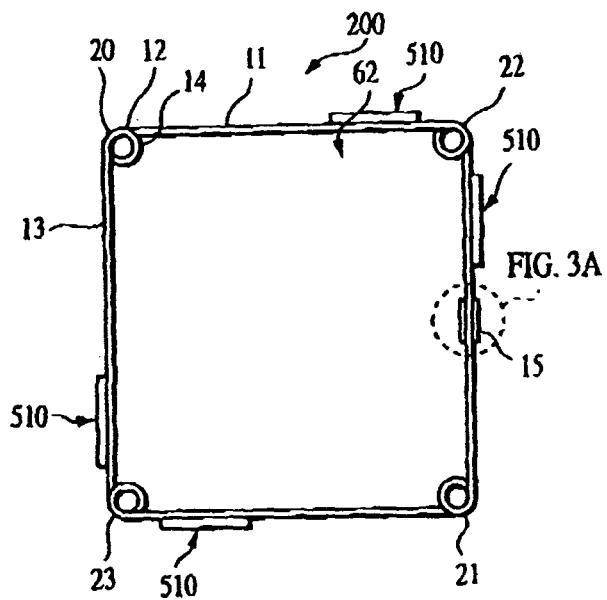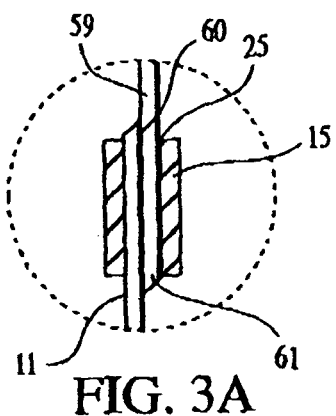
FIG. 3
FIG. 3A
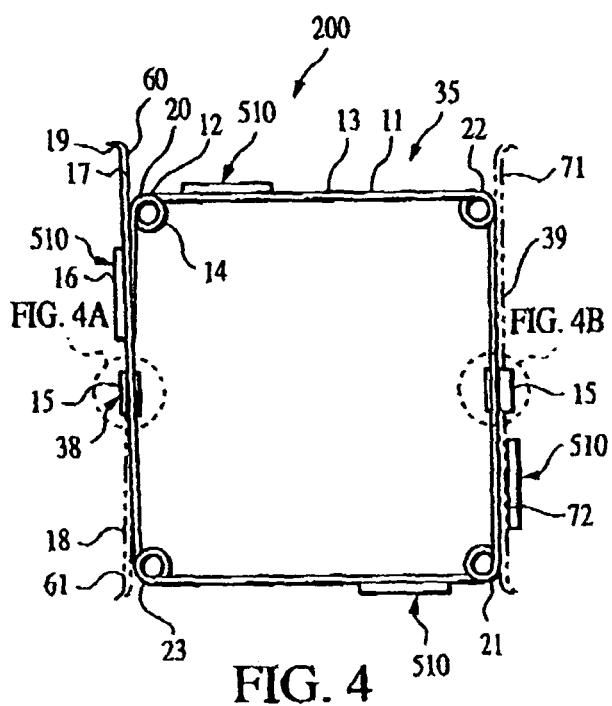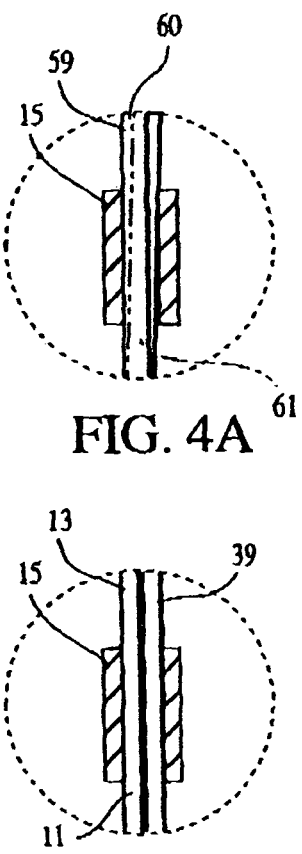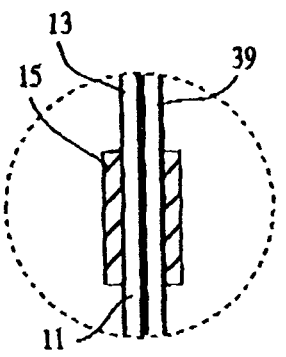
FIG. 4
FIG. 4A
FIG. 4B

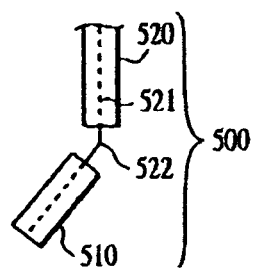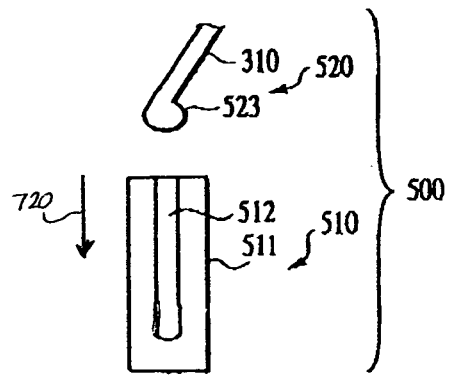
FIG. 9      FIG. 10
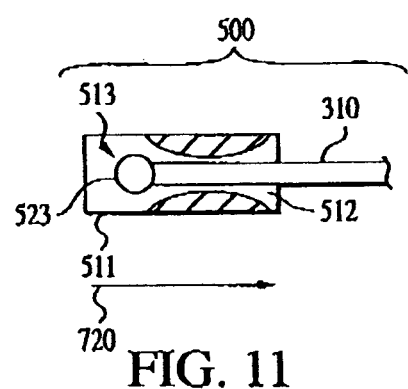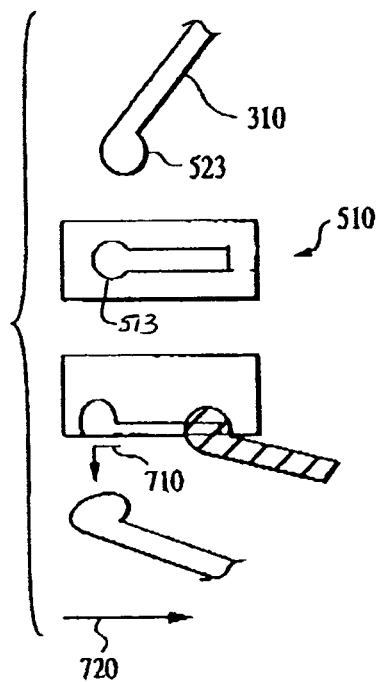
FIG. 11      FIG. 11A

RETRIEVABLE FILTER

REFERENCE TO EARLIER FILED APPLICATION

The present application claims the benefit of the filing date under 35 U.S.C. §119(e) of Provisional U.S. patent application Ser. No. 60/410,236, filed Sep. 12, 2002, which is hereby incorporated by reference.

BACKGROUND OF THE INVENTION

The present invention relates to a blood filtration unit which is to be implanted inside a vessel of a patient's body.

Currently known filtration units are formed by at least one filter which is implanted intravenously, generally into the inferior vena cava, to capture blood clots which could migrate towards the heart, in order to avoid the risk of embolism.

Traditionally, blood filters have been classified in two categories: permanent filters and temporary, or retrievable, filters.

Permanent filters are designed to be implanted permanently in patients where the risk of embolism is chronic. Some conventional permanent filters have, for example, a frustoconical structure comprising a series of branches terminated by barbs, anchors or similar structures which enable the filter to be secured permanently to the vessel wall. Long-term risks associated with implantation of a permanent vena cava filter include venous stasis due to caval occlusion and its related complications. Although long term complication rates with permanent filters in patients are low, these can be avoided with the use of retrievable or temporary filters in patients with indications such as after severe trauma, and prior to extensive orthopedic or pelvic surgery.

Temporary filters are designed to be implanted temporarily in patients where the risk of blood clot migration lasts only for a brief period, usually a few weeks. Temporary filters differ from permanent filters basically in that they do not comprise hooks for securing to the vessel wall. The branches of the filter simply engage the vessel wall without hooking into it. Several temporary filtering devices have been developed for insertion into the inferior vena cava (IVC) by transcatheter technique.

Temporary filters are further classified as either tethered temporary or retrievable filters. Tethered temporary filters are modified catheters or intraluminal devices attached to a tethering catheter or a wire for retrieval one to six weeks after implantation. Tethered filters remain connected throughout the entire period of implantation to prevent the filter from migrating in the vessel. They are implanted in the infrarenal vena cava with the tethering catheter extending out of the puncture site in the neck or groin, or buried subcutaneously within the soft tissues in the patient's neck. The tether remains coupled to the filter after deployment and is later used to retrieve the filter. The potential for septic complications associated with the tethering catheter exiting the neck or groin require removal of such devices within fourteen days of placement. Risk periods for pulmonary embolism in such patients, however, can extend up to twenty-one weeks.

Retrievable filters are usually self-expanding and self-attaching devices which can be removed or, if desired, left in place permanently. Typically, these filters have a construction similar to some versions of permanent filters. A hook or similar grasping structure is provided to allow a snare to engage the filter during the retrieval procedure. The filter in its entirety is then retrieved using a snare by drawing it into a catheter. However, to ensure the filter does not migrate within the vessel, barbs, anchors or similar structures must be used to engage the filter with the interior wall of the vessel for retaining the filter in place. These anchors make removal without injuring the vessel difficult. Percutaneous retrieval of these devices requires a new jugular and/or femoral vein catheterization. There is approximately a two week period for removal or repositioning of the filter before it becomes fixed to the caval wall by endothelization. Most existing filters are not easily or safely removable after they have remained in place for more than two weeks, and consequently longer term temporary filters which do not result in the likelihood of injury to the vessel wall upon removal are not available.

In some patients, the risk of embolism remains great and continues over time contrary to what was expected. If a temporary filter has been implanted first, it is generally necessary to remove the filter in order to replace it by a permanent filter if the two week time period for removal or repositioning of the filter has been exceeded.

These problems are overcome through the use of a filter having a broad range of clinical utility with a long-term implantation period and at the same time a long-term retrievability option.

BRIEF SUMMARY OF THE INVENTION

In a first aspect, the invention is a long-term retrievable, permanent filter for filtering solid and semi-solid materials from a liquid moving axially in a generally tubular vessel, said filter having two parts: a first part comprising a stent for positioning, engaging the vessel walls, and becoming incorporated by endothelial tissue; and a second part comprising a filter, said filter releasably coupled to said stent by a locking mechanism. After the risk of embolism has passed, the filter part may be retrieved using a catheter and snare. Alternatively, the filter may be left in place permanently if desired.

In another aspect, the invention is a long-term retrievable, permanent filter for filtering solid and semi-solid materials from a liquid moving axially in a generally tubular vessel comprising: (1) a stent for positioning, engaging the vessel walls, and becoming incorporated by endothelial tissue; (2) a filter; and (3) a locking mechanism for releasably coupling said stent to said filter; wherein said filter further comprises an apical hub, a plurality of divergent legs, at least one of said plurality of divergent legs secured at one end to said hub, at least one of said plurality of divergent legs releasably secured at another end, which is distally located with respect to said hub, to said stent by said locking mechanism. wherein said locking mechanism further comprises a stent attachment means and a filter attachment means.

In another aspect, the invention is a long-term retrievable, permanent filter for filtering solid and semi-solid materials from a liquid moving axially in a generally tubular vessel comprising: (1) a stent for positioning, engaging the vessel walls, and becoming incorporated by endothelial tissue; (2) a filter; and (3) a locking mechanism for releasably attaching said stent to said filter; wherein said filter further comprises an apical hub, a plurality of filter legs having an upstream end and a downstream end, at least one of said plurality of filter legs secured at the downstream end to said hub, at least one of said plurality of filter legs releasably secured at the upstream end to said stent by said locking mechanism.

In yet another aspect, the invention is a long-term retrievable, permanent filter for filtering solid and semi-solid materials from a liquid moving axially in a generally tubular vessel comprising: (1) a stent for positioning, engaging the vessel walls, and becoming incorporated by endothelial tissue; (2) a filter; and (3) a locking mechanism for releasably attaching said stent to said filter; wherein said filter further comprises an apical hub, a plurality of divergent legs having an upstream end and a downstream end, at least one of said plurality of divergent legs secured at the downstream end to said hub, at least one of said plurality of divergent legs releasably secured at the upstream end to said stent by said locking mechanism; wherein said locking mechanism further comprises stent attachment means attached to the downstream end of at least one of said plurality of divergent legs and at least one filter attachment means attached to said stent.

In yet another aspect, the invention is a long-term permanent retrievable filter for filtering solid and semi-solid materials from a liquid moving axially in a generally tubular vessel of a mammal comprising: (1) a filter comprising a plurality of divergent legs each having an upstream end and a downstream end, each of said plurality of divergent legs further comprising a cannula and a lumen; (2) an apical hub connecting each of said downstream ends of said plurality of divergent legs; (3) a stent configured to engage a wall of said generally tubular vessel and become incorporated by endothelial tissue; (4) a locking mechanism comprising a stent attachment means attached to said filter and a filter attachment means attached to said stent, said stent attachment means is releasably secured to said filter attachment means for releasably securing said filter to said stent, said stent attachment means further comprising at least one attachment wire, said at least one attachment wire extends through at least one lumen of said plurality of divergent legs and is attached at a retrieval connection point; wherein an upward motion applied to said retrieval connection point disengages said at least one attachment wire of said stent attachment means from said filter attachment means.

BRIEF DESCRIPTION OF SEVERAL VIEWS OF THE DRAWINGS

FIG. 3 depicts a plan view of one exemplary embodiment of the stent part of the long-term retrievable, permanent filter of FIGS. 1 and 2.

FIG. 3A depicts a plan view and enlarged, partial cross sectional view of the stent part of the long-term retrievable, permanent filter of FIG. 3.

FIGS. 4-4b depicts a plan view and enlarged, partial cross sectional views of a second embodiment of the stent part of the long-term retrievable, permanent filter of FIGS. 1 and 2.

FIG. 9 depicts an alternative preferred embodiment of a locking mechanism of the long-term retrievable, permanent filter of FIGS. 1 and 2.

FIG. 10 depicts another alternative preferred embodiment of a locking mechanism of the long-term retrievable, permanent filter of FIGS. 1 and 2.

FIG. 11 depicts another alternative preferred embodiment of a locking mechanism of the long-term retrievable, permanent filter of FIGS. 1 and 2.

FIG. 11A depicts another alternative preferred embodiment of a locking mechanism of the long-term retrievable, permanent filter of FIGS. 1 and 2.

DETAILED DESCRIPTION OF THE INVENTION

Figure 1:
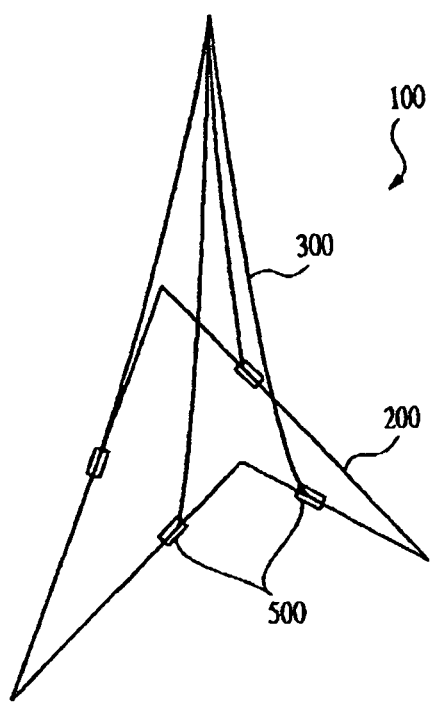
FIG. 1 depicts a perspective view of one embodiment of the long-term retrievable, permanent filter of the present invention.

As noted above, the present invention relates to a number of different aspects of a long-term, retrievable, permanent filter. Schematic illustrations of the preferred embodiments are provided in FIGS. 1-19A.

Referring to the drawings in detail, the invention as illustrated is embodied in a long-term retrievable, permanent filter 100 for filtering solid and semi-solid materials from a liquid moving axially in a generally tubular vessel 700 having two parts: a first part comprising a stent part 200 for positioning and engaging the vessel walls and becoming incorporated by endothelial tissue; and a second part comprising a filter part 300. A locking mechanism 500 releasably attaches the filter part 300 to the stent part 200. Preferably, locking mechanism 500 is a two part locking mechanism comprising a filter attachment means 510 and a stent attachment means 520, as described in further detail herein.

The stent part 200 of long-term retrievable, permanent filter 100 most preferably comprises a square stent as described herein. It is also anticipated that stents of the type described in U.S. Pat. No. 6,200,336, the disclosure of which is incorporated herein by reference, stents such as the Cook Z® Stent, stents of the type disclosed in U.S. Pat. Nos. 5,035,706 and 4,580,568, the disclosures of which are incorporated herein by reference, and other stents may be used in the alternative.

In the preferred embodiment shown in FIG. 3, stent part 200 comprises a multiple-sided stent comprising a frame 11 of resilient material, preferably metal wire made of stainless steel or a superelastic material (e.g., nitinol). Although the embodiments shown depict a round wire, other types of wire, e.g., flat, square, or triangular, may be used to form the frame.

In the illustrative embodiment, the frame 11 comprises a closed circumference 62 of a single piece of material 59 that is formed into a multiple-sided stent having a plurality of sides 13 interconnected by a series of bends 12. The preferred and depicted embodiment includes four sides 13 of approximately equal length. The square stent design provides optimal radial pressure and conformity to the vein wall with the least amount of metal and therefore achieves good anchoring and minimizes inflammatory responses. Alternative embodiments include forming a frame into any polygonal shape, for example a pentagon, hexagon, octagon, etc. In the preferred embodiments of FIG. 3 and 5, the bends 12 interconnecting sides 13 comprise a coil 14 of approximately one and a quarter turns. The coil bend is spring-like and reduces stress and metal fatigue. When using stainless steel wire, the size of the wire depends on the size of the device and the application. In one preferred embodiment of stent part 200, the wire is metal and, the wire is stainless steel and round. In such an embodiment, the diameter of the wire is between about 0.005 and about 0.020 inch, more preferably between about 0.012 and about 0.016 inch, and most preferably is about 0.012 inch. The frame 11 ranges in sizes from about 10 mm and about 50 mm, more preferably between about 30 and about 45 mm, and most preferably is about 35 mm. Wire that is too stiff can damage the vessel, not conform well to the vessel wall, and increase the profile of the device.

Returning to FIG. 3, the single piece 59 of material comprising frame 11 is formed into the closed circumference by securing the first and second ends 60, 61 with an attachment mechanism 15 such as a piece of metal cannula. The ends 60, 61 of the single piece 59 are then inserted into the cannula 15 and secured with solder 25, a weld, adhesive, or crimping to form the closed frame 11. The ends 60, 61 of single piece 59 can be joined directly without addition of a cannula 15, such as by soldering, welding, or other methods to join ends 60 and 61. Besides joining the wire, the frame could be fabricated as a single piece of material 59, by stamping or cutting the frame 11 from another sheet (e.g. with a laser), fabricating from a mold, or some similar method of producing a unitary frame.

Preferably, stent part 200 further includes one or more barbs 16 to anchor stent part 200 following deployment as shown in FIG. 4. As will be understood, a barb can be a wire, hook or any structure attached to the frame and so configured as to be able to anchor the stent part 200 within a lumen of a human or veterinarian patient. The illustrative embodiment includes a first barb 17 with up to three other barbs 18, 71, 72, indicated in dashed lines, representing alternative embodiments. As depicted in detail view 4A, each barb 17 and 18 of the barb combination 38 that comprises barbs 17 and 18 is an extension of the single piece 59 of material of the frame 11 beyond the closed circumference 59. The attachment cannula 15 secures and closes the single piece 59 of material into the frame 11 as previously described, while the first and second ends 60, 61 thereof, extend from the cannula 15, running generally parallel with the side 13 of the frame 11 from which they extend. Preferably, each end 60, 61 terminates around or slightly beyond respective bends 20, 23 to form barbs 17, 18, which anchors the stent 100 following deployment. More preferably, each barb 17, 18 extends about 1-2 mm over frame 11 on opposing bends 20, 23. To facilitate anchoring, the distal end 19 of barb 17 in the illustrative embodiment contains a bend or hook. Optionally, the tip of the distal end 19 can be ground to a sharpened point for better tissue penetration. Most preferably additional barbs 71, 72 are added to opposing corners 21, 22. To add a third and fourth barb as shown, a double ended barb 39 comprising barbs 71 and 72 is attached to the opposite side 13 as defined by bends 21 and 22.

Unlike barb combination 38, the double barb 39, as shown in detail view 4B, comprises a piece of wire, usually the length of barb combination 38, that is separate from the single piece 59 comprising the main frame 11. It is secured to the frame by attachment mechanism 15 using the methods described for FIG. 3. While this embodiment describes up to a four barb system, more than four barbs can be used.

The stent part 200 further includes a filter attachment means 510 for attaching the filter part 300 to the stent part 200 to form the long-term retrievable, permanent filter 100. Preferably, the filter attachment means 510 comprises at least one cannulae 510 attached to the frame 11 as shown in FIGS. 3 and 4. Most preferably, the filter attachment cannulae 510 are about 20 gauge ("G") or about 21 G.

The filter part 300 of the long-term retrievable, permanent filter 100 may be a filter of the type described in U.S. Pat. Nos. 4,580,568, 5,035,706, 5,133,733, the disclosures of which are incorporated herein by reference, filters such as the Cook Günther-Tulip™ Vena Cava filter as well as other vena cava filters.

Figure 6:
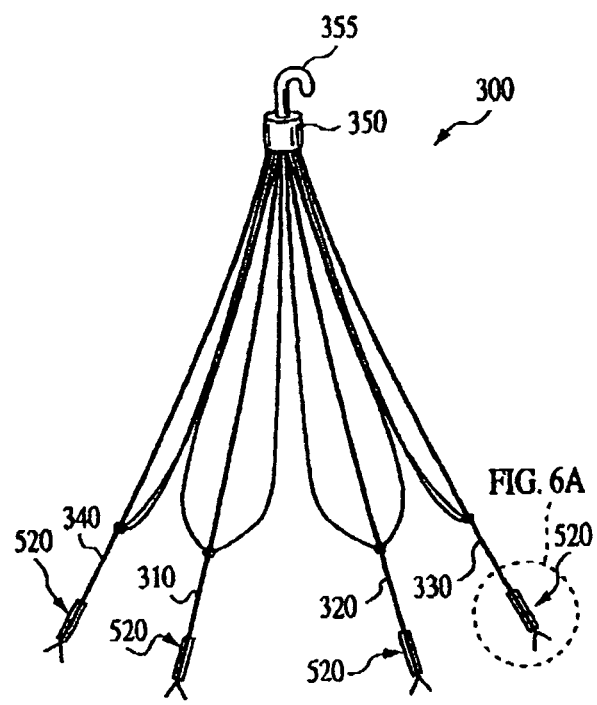
FIG. 6 depicts a side view of one preferred embodiment of the filter part of the long-term retrievable, permanent filter of FIGS. 1 and 2.
Figure 6A:
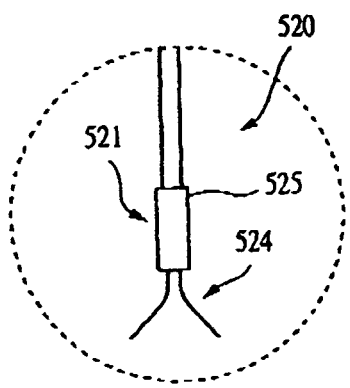
FIG. 6A depicts an enlarged, partial, side-view of a stent attachment means of the filter part of FIG. 6.

FIG. 6 shows one preferred embodiment the filter part 300 in the expanded position. In this embodiment, the filter part 300 comprises a plurality of elongated legs. Preferably, each of the plurality of elongated legs, of which there are four for example, is of equal length and is identically configured to the others. The legs 310, 320, 330 and 340 are collectively arrayed in a conical geometric configuration so that the legs converge to the apical hub 350 and are symmetrically spaced about a central axis extending through an apical hub 350. The apical hub, or end ferrule, 350 may be of the kind disclosed in U.S. Pat. No. 4,691,246. Alternatively, other apical hubs as known in the art are contemplated. Preferably, the apical hub points upstream in the direction of blood flow in the blood vessel of a patient. Preferably, the apical hub 350 comprises a retrieval connection point 355 at the apex of the filter part 300.

The filter legs 310-340 may be flexible wire and, in one preferred embodiment, the wires are metallic and round. In such an embodiment, the diameter of the wire may be between about 0.2 and about 0.4 millimeter, for example about 0.3 or about 0.35 millimeter.

Figure 8:
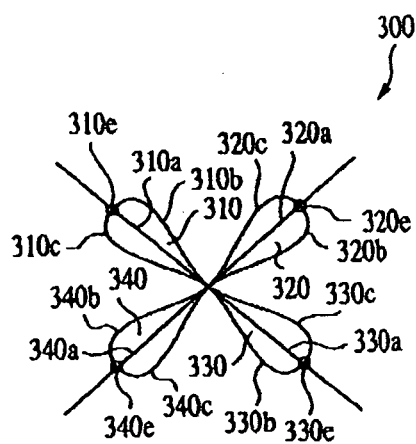
FIG. 8 depicts an end view of the filter part of FIG. 6.

Each leg comprises a central element 310a, 320a, 330a, 340a as well as two generally symmetrical curved side elements 310b, 320b, 330b and 340b and 310c, 320c, 330c and 340c extending on either side of each central element as best shown in FIG. 8. Each leg is distributed in a generally equally spaced angular manner so as to ensure the axial stability of the filter. As best seen in FIG. 6, preferably, the curvature of the four central wires is a flared, or trumpet shape, and the bends of the legs are aligned with one another around the periphery of the filter. The length and curvature of the legs 310-340 preferably are chosen such that after insertion into the blood vessel, the legs 310-340 are positioned to avoid contact with the wall of the blood vessel.

In the embodiment shown the two side elements of each leg 310-340 are formed from one piece of wire, the ends of which are held together in hub 350. At the middle of its length the wire piece may form an eyelet 310e, 320e, 330e, 340e surrounding the leg to be freely slidable along a part of the length thereof. Preferably, the side elements of each leg are formed from one piece of wire without the eyelet 310e-340e with the middle of the wire length attached to the leg as known in the art. By removing the eyelet 310e-340e, the potential that the wire crossing will be covered with neointima and potentially prevent retrieval is minimized. Preferably, the side elements of each leg have a length and a curvature such that, in the unfolded trumpet-like configuration of the filter part 300, the maximum distance between the side elements is of the same order as the distance between the neighboring side elements of two adjacent legs as shown in FIG. 8.

As shown in FIG. 6, at least one filter leg 310-340 further comprises a stent attachment means 520 for releasably engaging the filter attachment means 510 of the filter part 300.

In alternate embodiments, the filter part 300 may be formed without curved side elements 310b-340b, 310c-340c and may comprise a plurality of elongated legs with different lengths, thicknesses and flexibilities.

Coatings, such as biocompatible polymeric coatings, and surface treatments, such as metallization with a noble metal can be applied to the legs 310-340. Also, each of the legs 310-340 may be coated with a polymeric, synthetic resin material having anti-thrombogenic properties.

Figure 19:
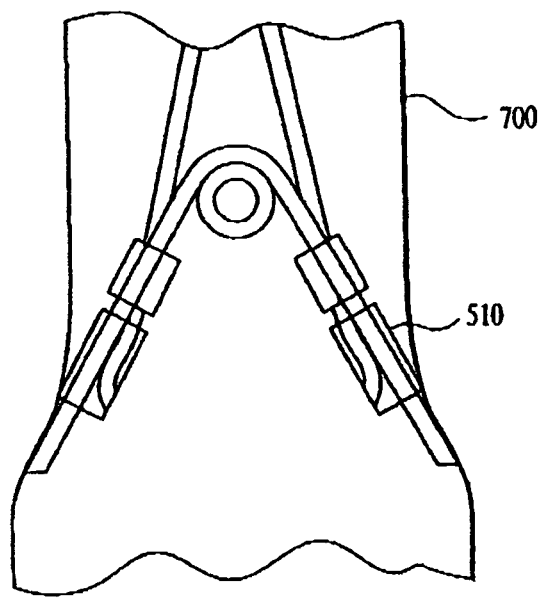
FIG. 19 depicts an enlarged, partial side view of the long-term retrievable, permanent filter of FIGS. 1 and 2 within a vein wall.
Figure 19A:
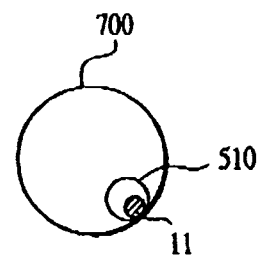
FIG. 19A depicts a partial, cross-sectional view of the long-term retrievable, permanent filter of FIG. 19.

The locking mechanism 500 comprises a filter attachment means 510 located on the stent part 200 and a stent attachment means 520 located on the filter part 300. The filter attachment means 510 releasably engages the stent attachment means 520, thereby releasably attaching the filter part 300 to the stent part 200. The locking mechanism 500 is sized to be large enough to remain locked during normal conditions, but small enough such that the force necessary to remove the filter part 300 does not damage the vessel during removal. It is believed that about 800 to about 1000 grams of force is the optimal force needed to remove the filter part 300 from the stent part 200. Preferably, locking mechanism directs the filter away from the wall of the lumen, as shown in FIGS. 1, 2, 19 and 19A. As shown in FIGS. 19 and 19A, preferably filter attachment means 510 protrudes into the lumen and away from the vein wall. The stent frame 11 and filter attachment means 510 are positioned adjacent to vein wall 700 such that stent attachment means 520 is positioned in an open area away from the vein wall 700. This configuration minimizes the risk of tissue in-growth at the connection points between the filter part 300 and anchor part 200.

In the embodiments shown in FIGS. 6-7, 9-13, the locking mechanism 500 may comprise an interference-fit locking mechanism. In these embodiments, the stent attachment means 520 comprises an attachment wire 521 and the filter attachment means 510 comprises a cannula 511. The attachment wire 521 may be an extension of the filter leg 310-340 or a separate piece of wire attached to the filter leg 310-340. Many different configurations have been contemplated for the attachment wire 521 of the stent attachment means 520 and the cannula 511 of the filter attachment means 510. For example, in the embodiment shown in FIG. 9, the attachment wire 521 of the stent attachment means 520 comprises a bend 522. In this embodiment, the bend 522 comprises an angle that provides a locking force when the filter part 300 is in the open or expanded configuration. When the filter part 300 is collapsed, however, the bend straightens and the locking force is reduced, thereby releasing the filter part 300 from the anchor part 200.

In the embodiment shown in FIG. 10, the attachment wire 521 of stent attachment means 520 comprises a ball 523 extending from the filter leg 310-340 and the cannula 511 of the filter attachment means 510 comprises a slot 512. In this embodiment, filter leg 310 is removed by sliding ball 523 through cannula slot 512. As shown in FIG. 11, the cannula 511, alternatively, may be crimped to form ball recess 513. FIG. 11 also shows that the ball 523 forms an interference fit with the cannula 511. FIG. 11A shows an alternate embodiment of filter leg 310 secured in place within cannula 511 of the filter attachment means 510. In this embodiment, filter leg is removed by sliding ball 523 into the ball recess 513 and away from cannula 511, as indicated by arrow 710. Preferably, the cannula slot 512 of the filter attachment means 510 coincides with the direction of blood flow (indicated by arrow 720 in FIGS. 11 and 11A) in the vessel. These configurations achieve a greater retention force in the direction of the blood flow than the amount of force required to push the filter into the cannula such that ball 523 of the stent attachment means 520 engages then ball recess 513 of the filter attachment means 510.

Figure 7:
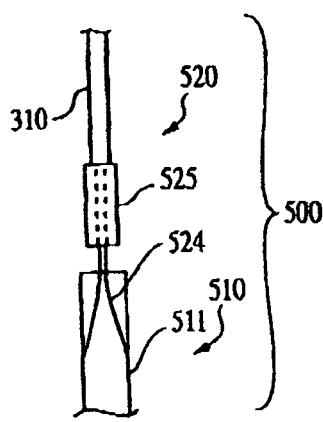
FIG. 7 depicts an enlarged, partial, side-view of one preferred embodiment of locking mechanism of the long-term retrievable, permanent filter of FIGS. 1 and 2.

In the embodiment shown in FIGS. 6 and 7, the attachment wire 521 of the stent attachment means 520 comprises a Y-shaped adapter and the filter attachment means 510 comprises a cannula 511. Preferably, the Y-shaped adapter further comprises a Y-shaped prong 524 attached to a cannula 525. The Y-shaped prong 524 was formed from 0.010 inch stainless steel wire. The stent attachment means 520 of the Y-shaped locking mechanism 500 is attached to the filter leg 310-340 at the end opposite the apical hub 350 by attaching the free end of the cannula 525 to the filter leg 310-340 by any means known in the art such as brazing, welding, soldering, crimping, mechanical fasteners, twisting, gluing and the use of adhesives etc.

Figure 12:
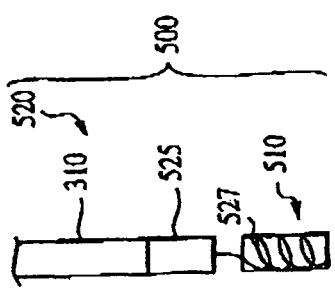
FIG. 12 depicts another alternative preferred embodiment of a stent attachment means of the long-term retrievable, permanent filter of FIGS. 1 and 2.

In an alternate embodiment shown in FIG. 12, the attachment wire 521 of the stent attachment means 520 comprises a looped adapter and the filter attachment means 510 comprises a cannula 511. Preferably, the looped adapter further comprises a looped wire 526 attached to a cannula 525. The looped adapter 526 forms an interference fit with the cannula 511.

Figure 13:
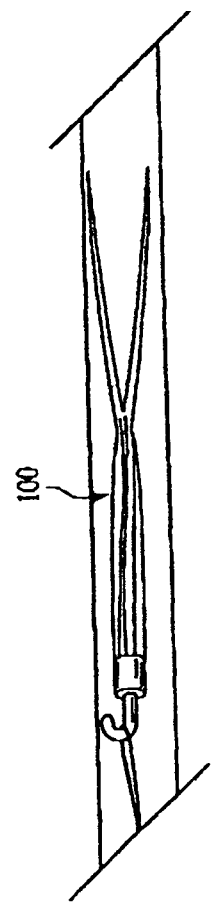
FIG. 13 depicts another alternative preferred embodiment of a locking mechanism of the long-term retrievable, permanent filter of FIGS. 1 and 2.

In yet another alternate embodiment shown in FIG. 13, the attachment wire 521 of the stent attachment means 520 comprises a coiled adapter and the filter attachment means 510 comprising a cannula 511. Preferably, the coiled adapter further comprises a coil 527 attached to a cannula 525.

Figure 14:
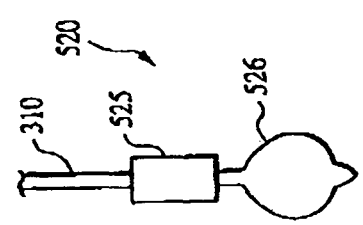
FIG. 14 depicts another alternative preferred embodiment of a locking mechanism of the long-term retrievable, permanent filter of FIGS. 1 and 2.

Still yet other embodiments of the locking mechanism 500 have been contemplated. In an alternate embodiment shown in FIG. 14, the locking mechanism 500 comprises a coiled locking mechanism. In this embodiment, the filter leg 310-340 comprises at least one coil 527 that attaches to a portion of the stent part 200. The coil 527 may releasably and directly engage a side of stent part 200. Alternatively, the coil 527 may releasably engage a loop 514 on the stent part 200 as shown in FIG. 14. In another embodiment, multiple coils may be used to vary the force required for removal. For removal, the filter part 300 is pulled by the retrieval connection point 355 and the coil 527 straightens and releases the stent part 200. In another embodiment, if the coil is formed from a shape memory alloy, the coil may be straightened by using localized heating or cooling.

Other locking mechanisms may be used to fix the free ends of the filter part 300 to the stent part 200 to form the long-term retrievable, permanent filter 100 of the present invention without departing from the spirit or scope of the present invention. For example, brazing, welding, soldering, crimping, mechanical fasteners, twisting, gluing and the use of adhesives etc. may be suitable for some applications. Alternatively, at least one leg 310-340 of filter part 300 can be modified to releasably attach to stent part 200 directly. In yet alternative embodiments, filter attachment means 510 may comprise an attachment wire and stent attachment means 520 may comprise a cannula. Any structure capable of directing the filter part 300 away from the wall of the lumen is contemplated.

Figure 2:
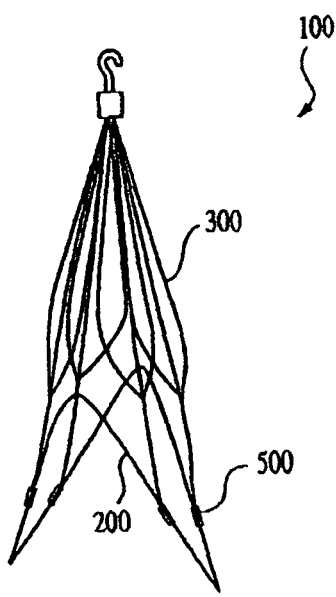
FIG. 2 depicts one preferred embodiment of the long-term retrievable, permanent filter of FIG. 1.
Figure 5:
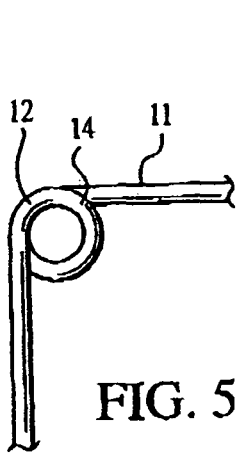
FIG. 5 depicts an enlarged, partial view of the embodiment of FIGS. 3 and 4-4b.
Figure 15:
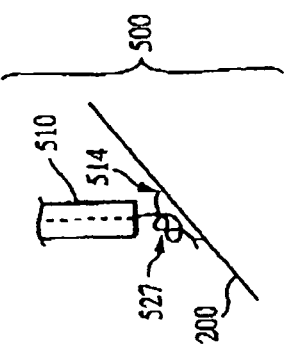
FIG. 15 depicts a partial, side-view of the long-term retrievable, permanent filter of FIGS. 1 and 2 retracted within an introduction catheter.

From the unfolded trumpet-like configuration illustrated in FIGS. 1 and 2, the long-term retrievable, permanent filter 100 may be collapsed into a slender and very narrow bundle of filter elements as shown in FIG. 15, the cross-sectional dimension of which is approximately equal to the sum of the thicknesses of the central and side elements of all four legs.

The locking mechanism 500 is designed such that the structure of filter part 300 remains in tact during the retrieval process. Therefore, in the collapsed configuration, the collected blood clots are retained within the filter part 300 as the filter part 300 is withdrawn into a collapsing sheath during the retrieval process. The locking mechanism 500 is also designed so that in the expanded configuration, the long-term retrievable, permanent filter 100 of the present invention provides a large retention force in the direction of the blood flow to retain the filter part 300 in place but is easily collapsed and retrieved without damaging the vein wall.

Figure 18:
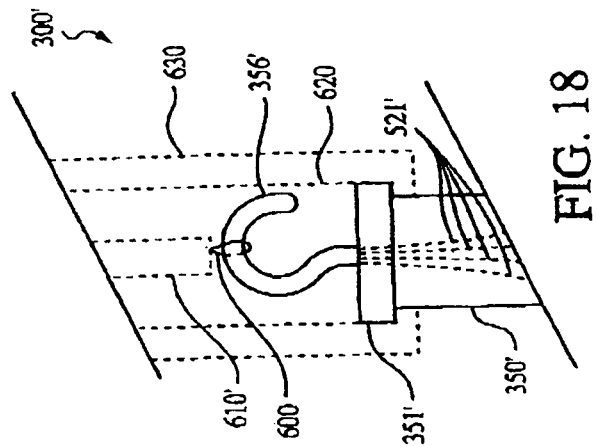
FIG. 18 depicts a side, partial cross-section view of an alternate preferred embodiment of the filter part of the long-term retrievable, permanent filter of FIGS. 1 partially within a collapsing sheath.
Figure 17:
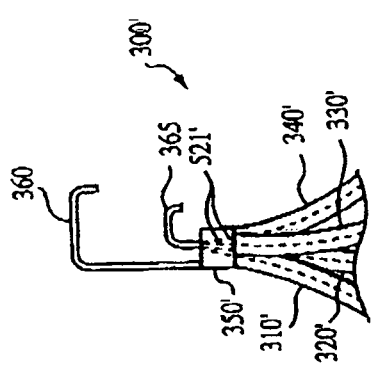
FIG. 17 depicts a side, partial cross-section view of another alternative preferred embodiment of the filter part of the long-term retrievable, permanent filter of FIG. 1.
Figure 16:
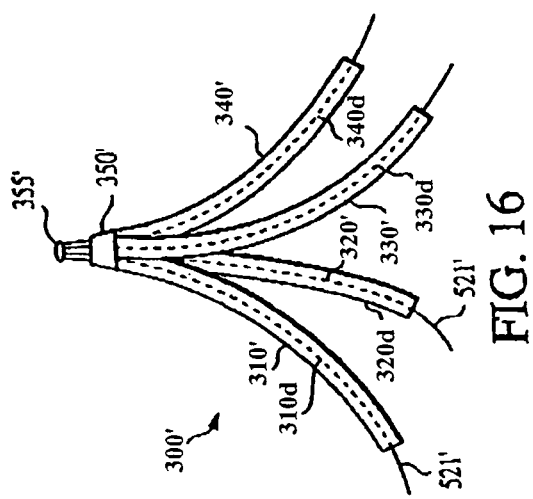
FIG. 16 depicts a side, partial cross-section view of another alternative preferred embodiment of the filter part of the long-term retrievable, permanent filter of FIG. 1.

FIGS. 16-18 show alternative preferred embodiments of the long-term, retrievable, permanent filter 100'. In these embodiments, the long-term retrievable, permanent filter 100' has been adapted such that the user can decrease the force required to unlock the filter part 300' from the stent part 200' to remove the filter part 300'. As seen in FIG. 16, at least one filter leg 3 10'-340' comprises a cannula and a lumen 310*d*, 320*d*, 330*d*, 340*d*. An apical hub 350' connects the filter legs 310'-340' to form the filter part 300'. The attachment wires 521' extend through lumens 310*d*, 320*d*, 330*d*, 340*d* and are attached at the retrieval connection point 355' of the filter part 300'. The retrieval connection point 355' may align with, or be positioned above, the apical hub 350'. As shown in FIG. 17, the apical hub 350' may further comprise an outer hook 360 and the retrieval connection point 355' may comprise an inner hook 365. The two hooks 360, 365 may be snared with a retrieval loop and squeezed together such that the upward motion of the inner hook 365 disengages attachment wires 521' of the stent attachment means 520 from the filter attachment means 510.

In the alternate preferred embodiment shown in FIG. 18, the apical hub 350' comprises a locking ring 351' and retrieval connection point 355' comprises a snare hook 356'. To disengage attachment wires 521' of the stent attachment means 520' from the filter attachment means 510'. A retrieval loop 600 is used to withdraw the snare hook 356' into a snare catheter 610 and in so doing secures the snare hook 356'. Next, an unlocking catheter 620 is advanced towards and positioned against the locking ring 351'. The retrieval loop 600 is then withdrawn to pull attachment wires 521' through filter legs 310'-340' and unlock the attachment wires 521' of the stent attachment means 520 from the filter attachment means 510. As the retrieval loop 600 is retracted, the filter part 300' is pulled within a collapsing sheath 630 and collapses.

In accordance with the invention, both the stent part 200 and the filter part 300 may be made of various materials, which can differ from each other, and can have different sizes and strengths. Preferably, the material is metal. Although the wire used in the preferred embodiments has a round cross-section, other shapes are also functional. In the preferred embodiment, the wire is preferably a radiopaque and non-ferromagnetic metal which has been certified for use in permanently implanted medical devices by the International Standards Organization (ISO). In particular, the wire may be made of a 316L stainless steel wire, or of a suitable grade of stainless steel such as that known as AFNOR K 13C20 N16 Fe15. Alternatively, the wire may be a high cobalt, low ferrous alloy, such as that known as and sold under the registered trademarks of "PHYNOX," "ELGILOY" or "Conichrome" which may have the composition, by weight percent: cobalt 42%, chromium 21.5%, nickel 18%, iron 8.85%, molybdenum 7.6%, manganese 2% with the balance made up of carbon and beryllium having a maximum of 0.15% carbon and 0.001% beryllium. Also, the wire may be a nickel-chromium alloys, such as "MP35N" or that known as and sold under the registered trademark of "Inconel." The wire may also be formed from titanium, titanium alloy, nickel titanium alloy known to be shape-memory metals which are sold and manufactured under the trademark "NITINOL", an alloy of tantalum or any other biocompatible material with elasticity may in certain circumstances be employed to advantage. When a nickel titanium alloy is used, the wires are operating in the linear portion of the stress/strain curve of the alloy, though it is possible to employ wires operating in the super-elastic region while obtaining benefits of the invention. Likewise, thermally responsive shape-memory metal can be employed with the geometric and spatial constraints provided by the invention. Alternatively, the wire may be formed from various polymers. It is also anticipated that new materials, as they are developed, will be useful.

Preferably, the long-term retrievable, permanent filter 100 of the present invention is preferably constructed from materials that will preferably withstand twelve million respiratory cycles without mechanical failure and will be non-thrombogenic.

A long-term retrievable, permanent filter 100 according to the invention is positioned in a blood vessel according to the conventional process which is facilitated by the flexibility of the filter. For percutaneous insertion of long-term retrievable, permanent filter 100, a vein is punctured with a needle, and a guidewire is advanced into the blood vessel through the needle beyond the desired implantation site. A catheter consisting of an inner, dilating cannula within an outer sheath, up to 14 French in diameter, is then advanced into the vein, over the guidewire. When the desired implantation site is reached, the inner dilating cannula and guidewire are removed, leaving the sheath behind. The sheath acts as a conduit to permit the insertion of the filter. The long-term retrievable, permanent filter 100, in a collapsed configuration, is introduced into the sheath and advanced to the implantation site as shown in FIG. 15. Once long-term retrievable, permanent filter 100 is in an appropriate position, the long-term retrievable, permanent filter 100 is pushed out of the sheath or uncovered using a pushing catheter. Upon discharge, the filter part 300 and the stent part 200 open, the stent part 200 positions the long-term retrievable, permanent filter 100 in the blood vessel and engages the interior wall of a blood vessel of a patient.

A long-term retrievable, permanent filter 100 according to the invention is retrieved from a blood vessel by advancing a guidewire into the blood vessel to the implantation site. Then, advancing a catheter over the guidewire to the retrieval connection point 355 of the filter part 300. The guidewire is withdrawn and a retrievable loop is advanced through the collapsing catheter to the retrieval connection point 355 of filter part 300. The retrieval connection point 355 is grasped by the retrievable loop. As the retrievable loop is withdrawn, locking mechanism 500 releases filter part 300 from stent part 200 and filter part 300 is collapsed within the collapsing catheter.

Whereas the long-term retrievable, permanent filter 100 of the present invention has been described and illustrated with reference to a specific embodiment comprising four legs and a square stent it will be understood that various modification, e.g., with respect to the number of legs and/or the configuration of the stent can be made without departing from the scope of the following claims.

The invention claimed is:

1. A retrievable filter for filtering solid and semi-solid materials from a liquid moving axially in a generally tubular vessel of a mammal comprising:

a) a filter comprising an apical hub and a plurality of divergent legs including first and second ends, at least one of the plurality of divergent legs being secured at the first end to the apical hub;

b) a first attachment member separate from, but attached to the second end of at least one of the plurality of divergent legs;

c) a stent; and d) a second attachment member separate from, but attached to the stent, the first and second attachment members being separate from, but attachable to one another to releasably attach the filter to the stent, wherein one of the first attachment member and the second attachment member comprises an attachment wire and wherein the attachment wire is positioned in a lumen of a tubular member.

2. The retrievable filter of claim 1 wherein the stent is configured to engage a wall of the generally tubular vessel and become incorporated by endothelial tissue.

3. The retrievable filter of claim 1 further comprising a retention force capable of withstanding the liquid moving axially in the generally tubular vessel and a retrieval force to detach the filter from the stent, wherein the retention force is greater than the retrieval force.

4. The retrievable filter of claim 1 wherein the filter is configured to maintain its structure when the filter is detached from the stent.

5. The retrievable filter of claim 1 wherein the filter is configured to maintain its structure when the first attachment member is detached from the second attachment member.

6. The retrievable filter of claim 1 wherein the filter is configured to avoid contact with the generally tubular vessel.

7. The retrievable filter of claim 1 wherein at least one of the first attachment member and the second attachment member is configured to position the filter to avoid contact with the generally tubular vessel.

8. The retrievable filter of claim 1 wherein at least one of the first attachment member and the second attachment member is configured to position at least one of the plurality of divergent legs to avoid contact with the generally tubular vessel.

9. The retrievable filter of claim 1 wherein at least one of the first attachment member and the second attachment member is configured to avoid contact with the tubular vessel.

10. The retrievable filter of claim 1 wherein the stent is a square stent.

11. The retrievable filter of claim 1 wherein the stent is self-expanding.

12. The retrievable filter of claim 1 wherein the first attachment member and the second attachment member form an interference fit.

13. The retrievable filter of claim 1 wherein the attachment wire further comprises an extension of one of the filter and the stent.

14. The retrievable filter of claim 1 wherein the attachment wire further comprises a bend.

15. The retrievable filter of claim 1 wherein the attachment wire further comprises a ball and one of the first attachment member and the second attachment member further comprises a slot and a ball recess.

16. The retrievable filter of claim 1 wherein the attachment wire comprises a Y-shaped adapter.

17. The retrievable filter of claim 16 wherein the Y-shaped adapter further comprises a Y-shaped prong.

18. The retrievable filter of claim 1 wherein the attachment wire comprises a looped adapter.

19. The retrievable filter of claim 18 wherein the looped adapter further comprises a looped wire.

20. The retrievable filter of claim 1 wherein the attachment wire comprises a coiled adapter.

21. The retrievable filter of claim 20 wherein the coiled adapter further comprises a coil.

22. The retrievable filter of claim 1 wherein at least one of the first attachment member and the second attachment member further comprises a coiled attachment member, the coiled attachment member comprising at least one coil.

23. The retrievable filter of claim 22 wherein the at least one coil is formed from a shape memory alloy.

24. The retrievable filter of claim 1 wherein the retrievable filter is configured so that a user can decrease the force required to detach the filter from the stent to remove the filter.

25. The retrievable filter of claim 1 further comprising a retrieval connection member and at least one attachment wire attached thereto;

wherein the at least one of the plurality of divergent legs further comprises at least one cannula and at least one lumen;

wherein the at least one attachment wire extends from the retrieval connection member and through the at least one lumen;

wherein the retrieval connection member further comprises a hook;

wherein the hook is configured so that an upward motion applied to the hook disengages the at least one attachment wire of the first attachment member from the second attachment member.

26. The retrievable filter of claim 25 wherein the apical hub further comprises an apical hook.

27. The retrievable filter of claim 25 wherein the apical hub further comprises a locking ring.

28. A retrievable filter for filtering solid and semi-solid materials from a liquid moving axially in a generally tubular vessel of a mammal comprising:

a) a filter comprising an apical hub and a plurality of divergent legs including first and second ends, at least one of the plurality of divergent legs being secured at the first end to the apical hub;

b) a first attachment member separate from, but attached to the second end of at least one of the plurality of divergent legs;

c) a stent; and d) a second attachment member separate from, but attached to the stent, the first and second attachment members being separate from, but attachable to one another to releasably attach the filter to the stent, wherein one of the first attachment member and the second attachment member comprises an attachment wire and wherein one of the first attachment member and the second attachment member comprises a cannula.

29. A retrievable filter for filtering solid and semi-solid materials from a liquid moving axially in a generally tubular vessel of a mammal comprising:

a) a filter comprising a plurality of divergent legs each having an upstream end and a downstream end, each of the plurality of divergent legs further comprising a cannula and a lumen;

b) an apical hub connecting each of the downstream ends of the plurality of divergent legs;

c) a first attachment member separate from, but attached to at least one of the plurality of divergent legs, the first attachment member including at least one attachment wire, the at least one attachment wire extends through at least one lumen of the plurality of divergent legs and is attached to a retrieval connection member;
d) a stent configured to engage a wall of the generally tubular vessel and become incorporated by endothelial tissue; and
e) a second attachment member separate from, but attached to the stent, the first and second attachment members being separate from, but attachable to one another to releasably attach the filter to the stent,
wherein an upward motion applied to the retrieval connection member disengages the at least one attachment wire of the first attachment member from the second attachment member.

30. A retrievable filter for filtering solid and semi-solid materials from a liquid moving axially in a generally tubular vessel of a mammal comprising:
   a filter comprising an apical hub and a plurality of divergent legs including first and second ends, at least one of the plurality of divergent legs being secured at the first end to the apical hub;
   a first attachment member separate from, but attached to the second end of at least one of the plurality of divergent legs;
   a stent comprising a frame including a closed circumference, the frame having a plurality of sides interconnected by a series of bends, each bend including a coil;
   a second attachment member separate from, but attached to the stent, the first and second attachment members being separate from, but attachable to one another to releasably attach the filter to the stent, at least one of the plurality of divergent legs of the filter being releasably secured at the second end to at least one of the plurality of sides of the stent by the first and second attachment members, wherein the filter and the stent are releasably secured to one another between an unattached position in which the first and second attachment members are not attached to one another and an attached position in which the first and second attachment members attach to one another; and
   wherein one of the first attachment member and the second attachment member comprises an attachment wire and wherein the attachment wire is positioned in a lumen of a tubular member.

* * * * *

UNITED STATES PATENT AND TRADEMARK OFFICE
CERTIFICATE OF CORRECTION

| | | |
|---|---|---|
| PATENT NO. | : 8,444,666 B2 | Page 1 of 1 |
| APPLICATION NO. | : 10/662216 | |
| DATED | : May 21, 2013 | |
| INVENTOR(S) | : Dusan Pavcnik et al. | |

It is certified that error appears in the above-identified patent and that said Letters Patent is hereby corrected as shown below:

On the Title Page

Left column, item (73) Assignee: Delete "Cook Medical Technologies LLC, Bloomington, IN (US)" and Insert --OREGON HEALTH & SCIENCE UNIVERSITY, Bloomington, IN (US)--

Signed and Sealed this
Twentieth Day of October, 2015

Michelle K. Lee
*Director of the United States Patent and Trademark Office*

UNITED STATES PATENT AND TRADEMARK OFFICE
CERTIFICATE OF CORRECTION

PATENT NO.           : 8,444,666 B2                                           Page 1 of 1
APPLICATION NO.      : 10/662216
DATED                : May 21, 2013
INVENTOR(S)          : Dusan Pavcnik et al.

It is certified that error appears in the above-identified patent and that said Letters Patent is hereby corrected as shown below:

On the Title Page

Left column, item (73) Assignee: Cook Medical Technologies LLC, Bloomington, IN (US)
and Insert --OREGON HEALTH & SCIENCE UNIVERSITY, Bloomington, IN (US)--

This certificate supersedes the Certificate of Correction issued October 20, 2015.

Signed and Sealed this
Twenty-sixth Day of January, 2016

Michelle K. Lee
*Director of the United States Patent and Trademark Office*